US011263577B2

(12) United States Patent
D'Amore (10) Patent No.: US 11,263,577 B2
(45) Date of Patent: *Mar. 1, 2022

(54) MOBILE VIEW FOR PHYSICIAN METRICS

(71) Applicant: CareFusion 303, Inc., San Diego, CA (US)

(72) Inventor: Tianyu D'Amore, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 127 days.

This patent is subject to a terminal disclaimer.

(21) Appl. No.: 16/675,095

(22) Filed: Nov. 5, 2019

(65) Prior Publication Data

US 2020/0074378 A1   Mar. 5, 2020

Related U.S. Application Data

(63) Continuation of application No. 15/036,788, filed as application No. PCT/US2014/065676 on Nov. 14, 2014, now Pat. No. 10,489,735.

(Continued)

(51) Int. Cl.
*G16H 40/20* (2018.01)
*G06Q 10/06* (2012.01)
*G16H 40/60* (2018.01)

(52) U.S. Cl.
CPC ....... *G06Q 10/06398* (2013.01); *G16H 40/20* (2018.01); *G16H 40/60* (2018.01)

(58) Field of Classification Search
CPC . G16H 40/20; G06Q 10/063; G06Q 50/22–24
See application file for complete search history.

(56) References Cited

U.S. PATENT DOCUMENTS

| 8,103,524 B1 | 1/2012 | Rogers et al. |
| 9,113,342 B1 | 8/2015 | Kotab |

(Continued)

FOREIGN PATENT DOCUMENTS

| CN | 1902650 A | 1/2007 |
| CN | 102299946 A | 12/2011 |

(Continued)

OTHER PUBLICATIONS

Chinese Office Action for Application No. 201480062615.5, dated Apr. 4, 2018, 24 pages.

(Continued)

*Primary Examiner* — John A Pauls
(74) *Attorney, Agent, or Firm* — Morgan, Lewis & Bockius LLP (57) ABSTRACT

A method that includes receiving a request on a mobile device from a user to access first performance data indicative of at least one performance metric of a physician is provided. The method includes receiving confirmation that the user has been authenticated as the physician and receiving the first performance data indicative of the at least one performance metric of the physician for a period of time. In some embodiments, the method further includes configuring the first performance data for display in a format specific to the mobile device and providing the formatted first performance data for display on the mobile device. A mobile device and a system to perform the above method are also provided.

20 Claims, 4 Drawing Sheets

Related U.S. Application Data (60) Provisional application No. 61/905,031, filed on Nov. 15, 2013.

(56) References Cited

U.S. PATENT DOCUMENTS

| | | |
|---|---|---|
| 2005/0085239 A1 | 4/2005 | Cedervall |
| 2006/0248062 A1 | 11/2006 | Libes et al. |
| 2008/0103815 A1 | 5/2008 | Beg |
| 2008/0133290 A1 | 6/2008 | Siegrist et al. |
| 2008/0177760 A1 | 7/2008 | Fein |
| 2009/0228330 A1 | 9/2009 | Karras et al. |
| 2010/0125474 A1* | 5/2010 | Harmon ............. G06Q 10/0639 705/7.38 |
| 2010/0218113 A1 | 8/2010 | White et al. |
| 2010/0293039 A1 | 11/2010 | Whitsitt et al. |
| 2012/0023163 A1 | 1/2012 | Mangold |
| 2012/0054119 A1 | 3/2012 | Zecchini |
| 2013/0173355 A1 | 7/2013 | Barcenas |
| 2013/0211731 A1 | 8/2013 | Woltman |
| 2013/0325617 A1 | 12/2013 | Delug |
| 2014/0278459 A1 | 9/2014 | Morris |

FOREIGN PATENT DOCUMENTS

| | | |
|---|---|---|
| CN | 102393871 A | 3/2012 |
| CN | 202711254 U | 1/2013 |

OTHER PUBLICATIONS

European Office Action for Application No. 14861820.0, dated Mar. 1, 2018, 8 pages.
Anonymous, "Reverse geocoding—Wikipedia", Mar. 10, 2013, XP055351349, Retrieved from the Internet: URL: https://en.wikipedia.org/w/index.php?title=Reverse_geocoding&oldid=543218853 [retrieved on Mar. 3, 2017] p. 1, paragraph 1.
Extended European Search Report for Application No. 14861820.0, dated Mar. 20, 2017, 8 pages.
International Search Report and Written Opinion for Application No. PCT/US2014/065676, dated Feb. 12, 2015, 11 pages.
Summons to attend oral proceedings pursuant to Rule 115(1) EPC for European Application No. 14861820.0, dated Nov. 5, 2018, 9 pages.
Chinese Office Action for Application No. 201480062615.5, dated Sep. 12, 2018, 28 pages with translation.
Chinese Office Action for Application No. 201480062615.5, dated May 15, 2019, 28 pages.
European Office Action for Application No. 14861820.0, dated Jun. 4, 2019, 21 pages.

* cited by examiner

MOBILE VIEW FOR PHYSICIAN METRICS

CROSS-REFERENCE TO RELATED APPLICATIONS

This application is a continuation application of U.S. application Ser. No. 15/036,788, entitled "MOBILE VIEW FOR PHYSICIAN METRICS," filed on May 13, 2016, now U.S. Pat. No. 10,489,735, which claims the benefit of International Application Serial No. PCT/US2014/065676, entitled "MOBILE VIEW FOR PHYSICIAN METRICS," filed on Nov. 14, 2014, which claims the benefit of U.S. Provisional Application Ser. No. 61/905,031, entitled "MOBILE VIEW FOR PHYSICIAN METRICS," filed on Nov. 15, 2013, the entirety of each of which is incorporated herein by reference.

BACKGROUND

Field

The present disclosure generally relates to the presentation of data, and more particularly to the use of a computing device to display data.

Background

Caregivers and healthcare personnel, such as physicians, are subject to high pressure in an ever increasingly competitive healthcare market. Patients and insurance providers are constantly reviewing healthcare professional performance and make decisions and selections accordingly. Thus, it is desirable for a healthcare provider or physician to have easy access to his or her personal performance data, in order to improve it. Also, it is desirable for managers and supervisors to have access to other healthcare professional's performance data for accountability and other managerial decisions such as compensation, costs, and billing.

SUMMARY

A computer-implemented method according to embodiments disclosed herein includes receiving a request on a mobile device from a user to access first performance data indicative of at least one performance metric of a physician. The method also includes receiving confirmation that the user has been authenticated as the physician and receiving the first performance data indicative of the at least one performance metric of the physician for a period of time. In some embodiments, the method further includes configuring the first performance data for display in a format specific to the mobile device and providing the formatted first performance data for display on the mobile device.

A system as disclosed herein includes a memory storing executable instructions and a processor configured to execute the executable instructions stored in the memory. Upon execution of the commands, the processor causes the system to receive a request on a mobile device from a user to access first performance data indicative of at least one performance metric of a physician. The processor may also cause the system to receive confirmation that the user has been authenticated as the physician, and to receive the first performance data indicative of the at least one performance metric of the physician for a period of time. In some embodiments, the processor also causes the system to configure the first performance data for display in a format specific to the mobile device and to provide the formatted first performance data for display on the mobile device, wherein the at least one performance metric is configured by the user.

A mobile device according to some embodiments includes a memory configured to store commands, a display configured to provide a plurality of metrics related to a healthcare professional's performance, and a communications module configured to communicate with a remote server through a network. The mobile device may also include a processor configured to execute the commands in the memory and retrieve a healthcare professional performance data from the remote server using the communications module, the processor is further configured to provide a graphic display of the healthcare professional performance data to the display. In some embodiments, the mobile device includes a geo-locator module configured to obtain at least two geo-coordinates for the mobile device, and to provide the at least two geo-coordinates to the processor.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed system provides for a display of metrics related to a healthcare professional's performance, on an electric device. In some embodiments, the electric device is a mobile device capable of communicating with a remote server through a network. The mobile device may be a smart phone, or a tablet device configured to wirelessly couple with the network. The network may be a local area network (LAN), a campus area network (CAN), a metropolitan area network (MAN), a wide area network (WAN), a broadband network (BBN), the Internet, and the like. Further, the network can include, but is not limited to, any one or more of the following network topologies, including a bus network, a star network, a ring network, a mesh network, a star-bus network, tree or hierarchical network, and the like.

As discussed herein, examples are provided in which the healthcare professional is a physician. It is understood, however, that the metrics provided for display can be for other healthcare professionals (e.g., pharmacists, nurses, technicians, assistants) for whom metrics in a healthcare setting are of particular relevance. In an effort to reduce spending and increase efficiency, a hospital or other healthcare institution may desire to make its physicians aware of their performance, as well as the performance of other physicians. The physician's performance may be judged by certain metrics. A device on which to deliver and display the metrics may be a mobile device.

Figure 1:
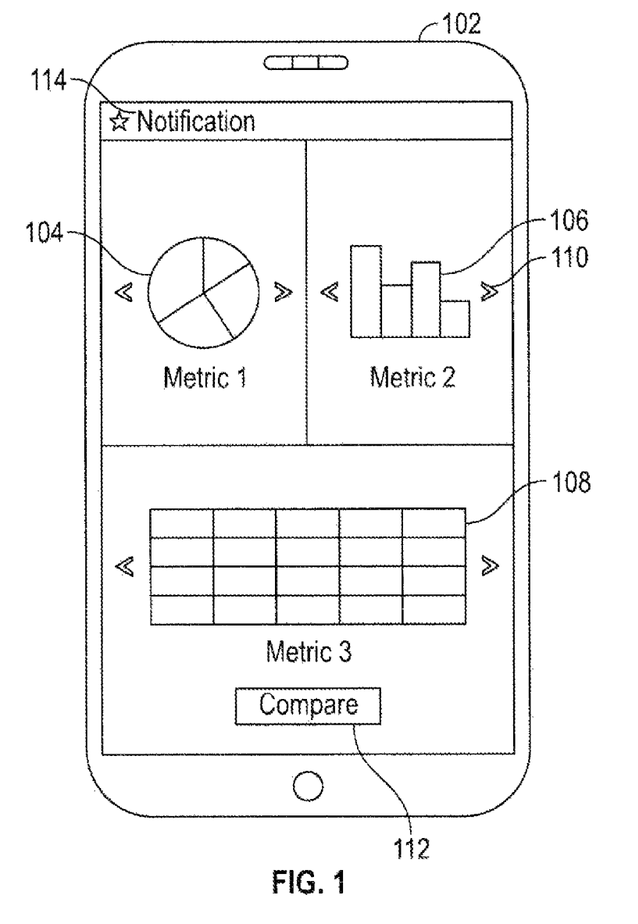
FIG. 1 illustrates an example embodiment of an example user interface for viewing physician metrics on a mobile device.

In one embodiment, and with reference to FIG. 1, physician metrics are provided for display on a user (e.g., physician or other healthcare professional) mobile device 102. The physician metrics may be provided for display after the user provides an authentication to access the user's physician metrics. The physician metrics generally pertain to physician performance, including cost and efficiency. Example physician metrics available for display are patient length of stay, average length of stay, cost per stay, mortality rate, readmission rate, case mix index, number of encounters, average daily checkout, average drug events, supply statistics, patient recovery time, medication spending, and patient satisfaction ratings. The physician metrics may be those associated with the user or other users.

The physician metrics are based on physician performance data, which is stored on a database (e.g., a knowledge portal, an evidence-based monitoring system such as Med-Mined®, etc.). Physician performance data may be any data related to the performance of the physician, including, but not limited to, physician data, patient data, medicine data, medical procedure data, hospital data, and feedback data.

A first physician metric 104, a second physician metric 106, and a third physician metric 108 are displayed. In certain aspects, any number of one or more physician metrics may be displayed. In certain aspects, the user is able to customize which physician metrics are displayed. In certain aspects, a default set of one or more physician metrics is initially displayed, which the user may then configure to create a customized display. In certain aspects, the default set of one or more physician metrics may change. For example, the set of physician metrics displayed on the mobile device 102 may change based on a location of the mobile device 102. The mobile device 102 may display a first set of physician metrics when the user is in his/her office. The mobile device 102 may display a second set of physician metrics when the user is in his/her home. The mobile device 102 may display a third set of physician metrics when the user is in a hospital. As another example, the set of physician metrics displayed on the mobile device 102 may change based on the user's specialty or area of care. A pediatrician's device may display a default set of physician metrics that is different than a cardiologist's default set of physician metrics.

The first physician metric 104 is displayed using a pie chart. The second physician metric 106 is displayed using a bar graph. The third physician metric 108 is displayed using a table. In certain aspects, the physician metric may be displayed in any number of styles. Example styles are a bar graph, a pie chart, a line graph, a table, a scatter chart, an area chart, a doughnut chart, a bubble chart, a radar chart, a surface chart, a stock chart, and a list. The metrics can display one or many user metrics within the same style (e.g., within the same graph or chart).

The user may select a different set of physician performance data to calculate the physician metric using an arrow 110 next to the physician metric display. In certain aspects, using the arrow 110 results in a display of a different set of physician performance data for the same physician metric. In certain aspects, using the arrow 110 results in display of a different physician metric. In certain aspects, instead of pressing an arrow, the user may swipe the screen over the physician metric in order to scroll to a different set of physician performance data.

The displayed metrics associated with a physician may be refreshed periodically to incorporate new data. For example, the displayed metrics may be refreshed in intervals of seconds, minutes, hours, days, weeks, months, or years. In certain aspects, the refresh frequency may be set by the user. The refresh frequency may be configured based on notification or data "fatigue" experienced by users when data is refreshed either too quickly or too slowly.

The user may access an interface comparing him/her to other physicians using the compare button 112. In certain aspects, using the compare button 112 causes a chart to be displayed. In certain aspects, the chart compares the user to other physicians, sorted by one or more physician metrics. In certain aspects, the chart ranks a set of physicians by a criterion. In certain aspects, the set of physicians is all physicians. In certain aspects, the set of physicians is the physicians in the same practice area as the user. In certain aspects, the criterion may be a single physician metric or a combination of two or more physician metrics. Data among physicians within the same care or in different care areas may be normalized for consistency.

The system may also generate notifications 114 informing the user of updates. Examples of updates include updated performance related data and updated rankings of the set of physicians.

The content available for display on the mobile device may vary, depending on the user. There may be limits placed on the access the user has to certain information. There may also be options that allow for the physician to approve or disapprove of access to physician performance data.

In certain aspects, the user may view the physician metrics associated with only the user. In certain aspects, the user may view the physician metrics associated with the user and other physicians. In certain aspects, a hospital administrator may view the physician metrics associated with all physicians. In certain aspects, the user may choose to opt-out, and that physician's performance data may no longer be used to generate physician metrics. Further, that physician's individual physician metrics may also no longer be available for comparison by other physicians. In certain aspects, the user may choose to opt-in, in order for that physician's performance data to be used to generate physician metrics, and for comparison by other physicians.

Figure 2:
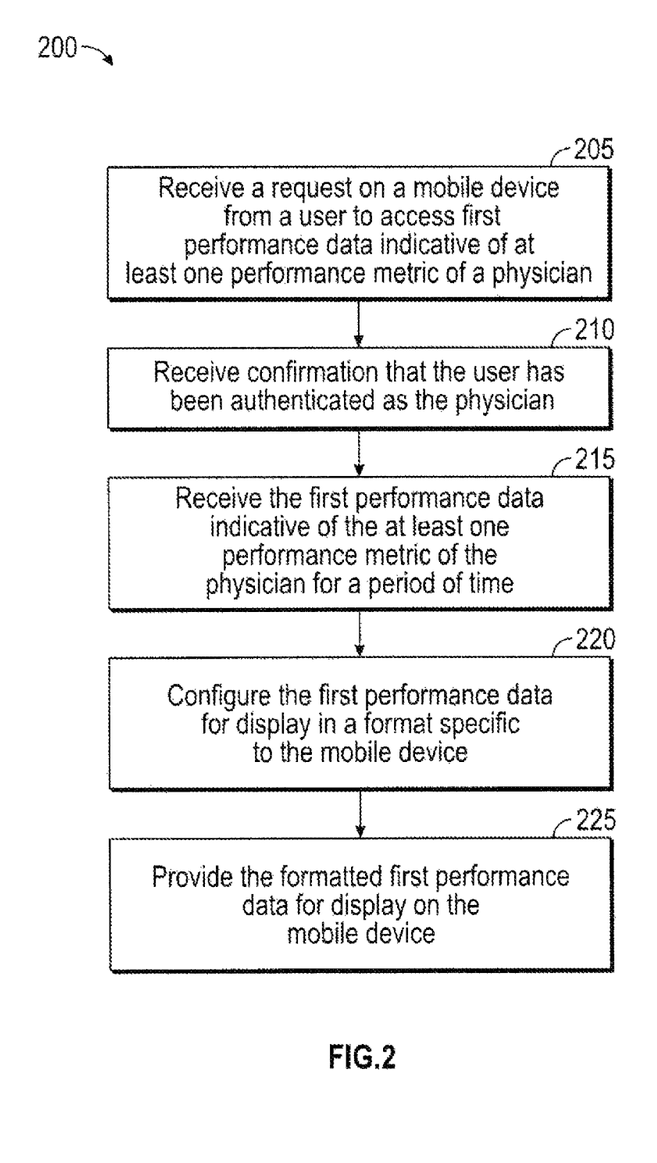
FIG. 2 illustrates an example process for viewing physician metrics on a mobile device.

FIG. 2 illustrates an example process 200 for viewing physician metrics on a mobile device. The process 200 begins at step 205 when a request is received on a mobile device (e.g., mobile device 102) from a user to access performance data indicative of at least one performance metric of a physician. The performance data, as previously discussed, are physician metrics that generally pertain to physician performance, including cost and efficiency.

In step 210, confirmation is received that the user has been authenticated as the physician. The authentication may be received from a server that also provides access to the performance data. This user authentication, as previously discussed, affects access to performance data and the content available for display on the mobile device (e.g., mobile device 102).

In step 215, performance data is received that is indicative of the at least one performance metric of the physician for a period of time.

In step 220, the performance data is configured for display in a format specific to the mobile device. For example, in the example user interface illustrated by FIG. 1, the performance data was configured for display in a pie chart 104, a bar graph 106, and a table 108 that is formatted for display on smaller displays such as those available in most mobile devices. Accordingly, in some embodiments step 220 includes configuring the performance data for display according to an orientation of the mobile device, such as a vertical or horizontal orientation, and selecting between a portrait or landscape aspect ratio of the display.

In step 225, the formatted performance data is provided for display on the mobile device (e.g., mobile device 102).

Figure 3:
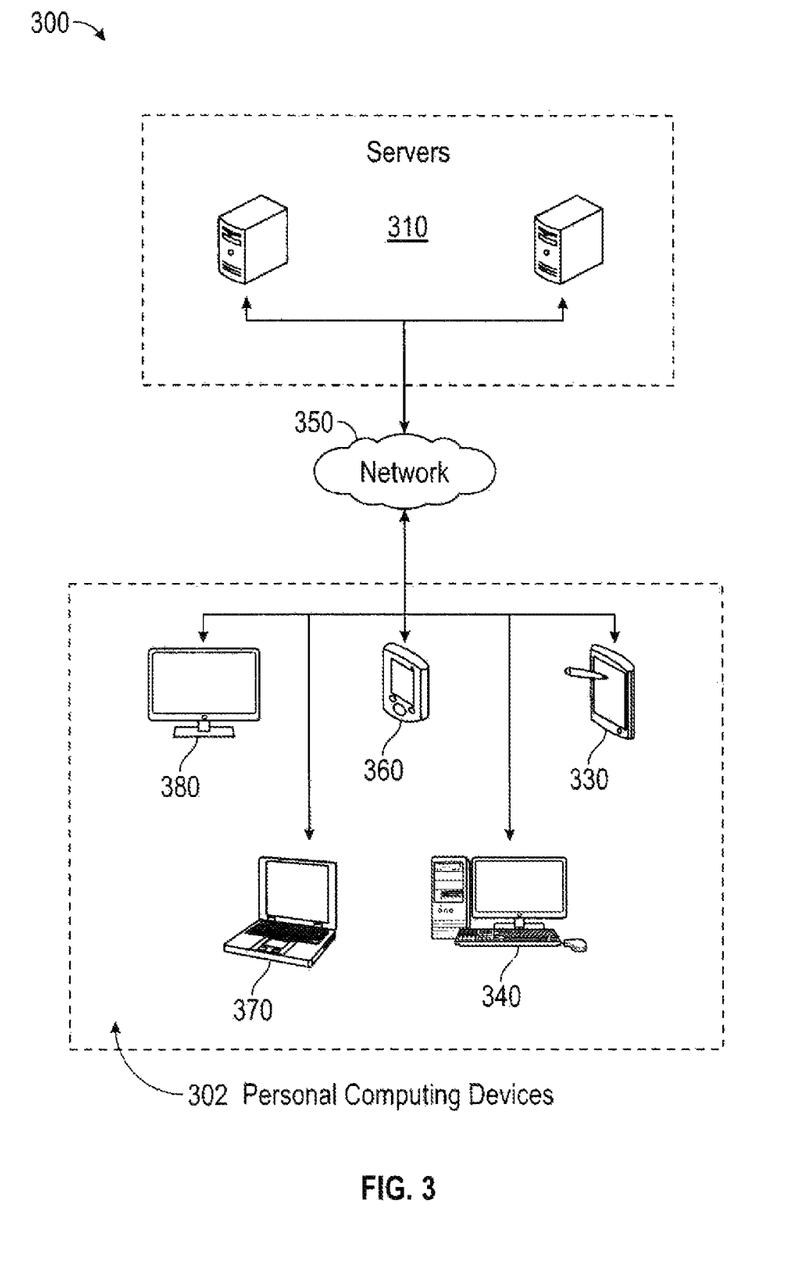
FIG. 3 illustrates an example architecture for providing a user interface for viewing physician metrics on a mobile device, according to some embodiments.

FIG. 3 illustrates an example architecture 300 for providing a user interface for viewing physician metrics on a mobile device, according to some embodiments. Architecture 300 includes servers 310 and personal computing devices 302 connected over a network 350. Each of the many personal computing devices 302 is configured to include and execute at least a network based application for displaying content. The network based application can be, for example, a web browser, a document or text editing program, an image editing program, a video editing program, a gaming program, a media player program, a social networking program, or any other program that displays content. The content can be, for example, a plurality of physician metrics provided by at least one of servers 310, a web page, a document, an image, a video, an audio file, a game, or other displayable content. Personal computing devices 302 can be, for example, a tablet computer 330 (e.g., including e-book readers), a desktop computer 340, a mobile device 360 (e.g., a smartphone or PDA), a personal computer device 370, a set top box 380 (e.g., for a television), a convertible device (e.g., tablet-to-laptop computer device) or any other devices having appropriate processor, memory, and communications capabilities for displaying content. More particularly, personal computing devices 302 may be associated with registered clients of one or more of servers 310. In that regard, any one of personal computing devices 302 may include all the features and characteristics of mobile device 102, described in detail above. Furthermore, any one of personal computing devices 302 can be used to perform at least one, or all of the steps in method 200, described above. Moreover, the steps in method 200 may be performed by personal computing device 302 communicating with any one of servers 310.

In certain aspects, the content for display in the application can be obtained from one or many servers 310 over network 350. Servers 310 can be any device having an appropriate processor, memory, and communications capability for hosting the content for display. The network 350 can include, for example, any one or more of a personal area network (PAN), a local area network (LAN), a campus area network (CAN), a metropolitan area network (MAN), a wide area network (WAN), a broadband network (BBN), the Internet, and the like. Further, the network 350 can include, but is not limited to, any one or more of the following network topologies, including a bus network, a star network, a ring network, a mesh network, a star-bus network, tree or hierarchical network, and the like.

Any one of personal computing devices 302 may include a memory configured to store commands, a display configured to provide a plurality of metrics related to a healthcare professional's performance, and a communications module configured to communicate with a remote server through a network. Any one of personal computing devices 302 may also include a processor configured to execute the commands in the memory and retrieve a healthcare professional performance data from the remote server using the communications module. In some embodiments, the processor is further configured to provide a graphic display of the healthcare professional performance data to the display. In some embodiments, any one of personal computing devices 302 includes a geo-locator module configured to obtain at least two geo-coordinates for the mobile device, and to provide the at least two geo-coordinates to the processor.

In some embodiments, any one of personal computing devices 302 includes a sensor module configured to determine an orientation of the personal computing device and provide the orientation to the processor to adjust the display in at least one of a horizontal or vertical configuration. Moreover, any one of personal computer devices 302 in any of the above configurations may include a geo-locator module that provides location information to the processor, the location information including whether the user is in one of a home or a hospital. The display in any one of personal computing devices 302 above may include a touch sensitive screen configured to receive input from a user, the input from the user including an authentication credential for the user to access the plurality of metrics related to the healthcare professional's performance.

The processor in any one of personal computing devices 302 above may adjust the display according to a user's specialty area of care. In that regard, any one of servers 310 may provide the user specialty area of care to any one of personal computing devices 302 upon certifying the authentication credential provided by the user.

Figure 4:
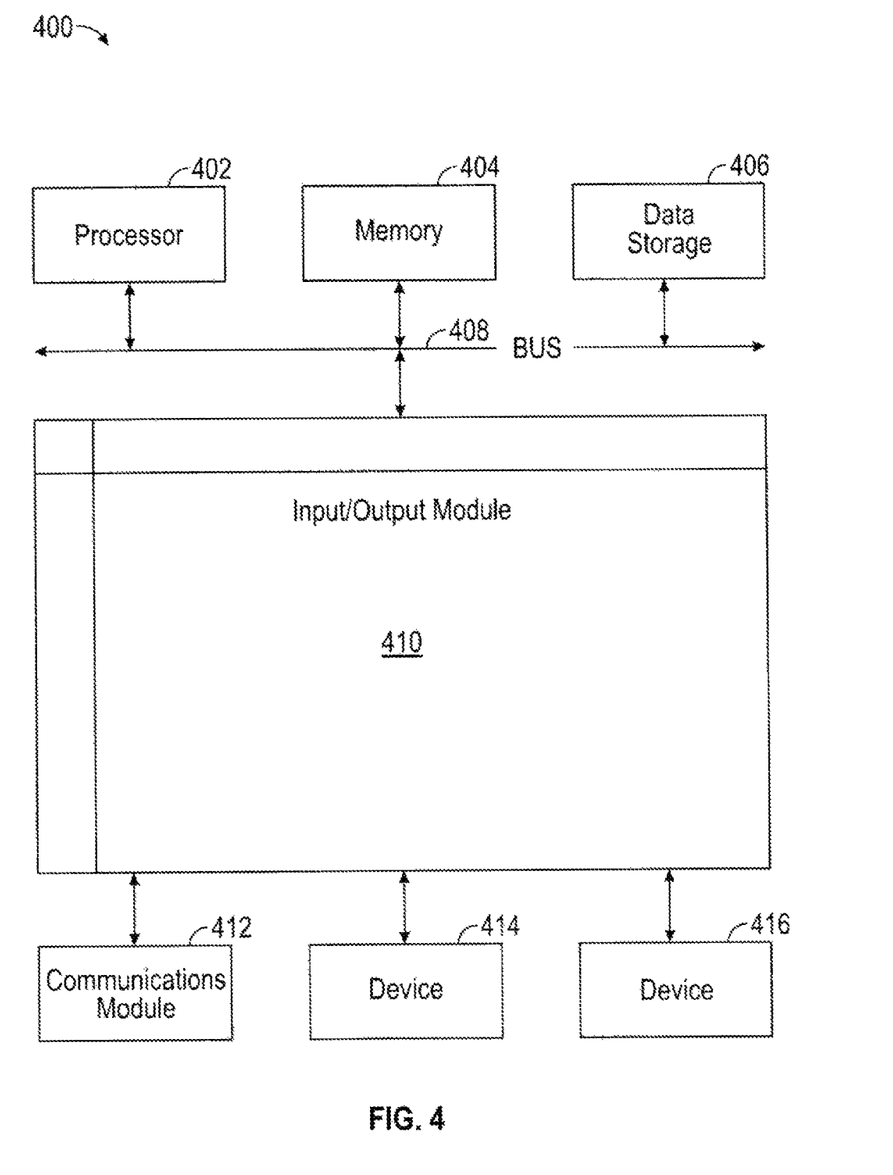
FIG. 4 is a block diagram illustrating an example computer system with which the personal computing device and server of FIG. 1 can be implemented.

FIG. 4 is a block diagram illustrating an example computer system 400 with which the personal computing device and server of FIG. 3 can be implemented. Also, mobile device 102 in FIG. 1, and method 200 in FIG. 2 can be implemented with computer system 400. In certain aspects, computer system 400 can be implemented using hardware or a combination of software and hardware, either in a dedicated server, integrated into another entity, or distributed across multiple entities.

Computer system 400 (e.g., personal computing devices 302 and servers 310) includes a bus 408 or other communication mechanism for communicating information, and a processor 402 coupled with bus 408 for processing information. By way of example, computer system 400 can be implemented with one or more processors 402. Processor 402 can be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 400 includes, in addition to hardware, code that creates an execution environment for the computer program in question, e.g., code that constitutes processor firmware, a protocol stack, a database management system, an operating system, or a combination of one or more of them stored in an included memory 404, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 408 for storing information and instructions to be executed by processor 402. Processor 402 and memory 404 can be supplemented by, or incorporated in, special purpose logic circuitry.

The instructions may be stored in memory 404 and implemented in one or more computer program products, i.e., one or more modules of computer program instructions encoded on a computer readable medium for execution by, or to control the operation of, the computer system 400, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, Wirth languages, embeddable languages, and xml-based languages. Memory 404 may also be used for storing temporary variable or other intermediate information during execution of instructions to be executed by processor 402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 400 further includes a data storage device 406 such as a magnetic disk or optical disk, coupled to bus 408 for storing information and instructions. Computer system 400 is coupled via input/output module 410 to various devices. The input/output module 410 is any input/output module. Example input/output modules 410 include data ports such as USB ports. The input/output module 410 is configured to connect to a communications module 412. Example communications modules 412 include networking interface cards, such as Ethernet cards and modems. In certain aspects, the input/output module 410 is configured to connect to a plurality of devices, such as an input device 414 and/or an output device 416. Example input devices 414 include a keyboard and a pointing device, e.g., a mouse or a trackball, by which a user can provide input to the computer system 400. Other kinds of input devices 414 are used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 416 include display devices, such as a LED (light emitting diode), CRT (cathode ray tube), or LCD (liquid crystal display) screen, for displaying information to the user.

According to one aspect of the present disclosure, personal computing device 302 can be implemented using a computer system 400 in response to processor 402 executing one or more sequences of one or more instructions contained in memory 404. Such instructions may be read into memory 404 from another machine-readable medium, such as data storage device 406. Execution of the sequences of instructions contained in main memory 404 causes processor 402 to perform the process steps described herein. One or more processors in a multi-processing arrangement may also be employed to execute the sequences of instructions contained in memory 404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 350) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 400 includes servers and personal computer devices, such as servers 310 and personal computing devices 302, described in detail above. A personal computing device and server are generally remote from each other and typically interact through a communication network. The relationship of client and server arises by virtue of computer programs running on the respective computers and having a client-server relationship to each other. Computer system 400 can be, for example, and without limitation, a desktop computer, laptop computer, or tablet computer. Computer system 400 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 402 for execution. Such a medium may take many forms, including, but not limited to, non-volatile media, volatile media, and transmission media. Non-volatile media include, for example, optical disks, magnetic disks, or flash memory, such as data storage device 406. Volatile media include dynamic memory, such as memory 404. Transmission media include coaxial cables, copper wire, and fiber optics, including the wires that comprise bus 408. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be disclosed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially disclosed as such, one or more features from a disclosed combination can in some cases be excised from the combination, and the disclosed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following disclosure. For example, the actions recited in the disclosure can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the disclosure.

The invention claimed is:

1. A computer-implemented method comprising:
    receiving a request via a mobile device for first performance data associated with a physician; the first performance data associated with a period of time;
    receiving the first performance data and a location of the mobile device;
    selecting, based on the location of the mobile device, a first set of physician metrics of a plurality of sets of physician metrics for display based on the first performance data in a format specific to the mobile device, the plurality of sets of physician metrics including two or more of patient length of stay, cost per stay, mortality rate, readmission rate, drug events, patient recovery time, medication spending, and patient satisfaction associated with the physician;
    providing the formatted first set of physician metrics for display on the mobile device;
    receiving an indication of an interaction with a portion of the mobile device presenting the displayed first set of physician metrics; and
    responsive to receiving the indication, switching the first set of physician metrics from using the first performance data to second performance data of a type of performance data different than a type of the first performance data, and displaying the same first set of physician metrics using the second performance data, the types of first and second performance data being selected from physician data, patient data, medicine data, medical procedure data, and hospital data.

2. The computer-implemented method of claim 1, further comprising:
    receiving an indication that the location of the mobile device is associated with the physician,
    wherein the selecting is based on the location being associated with the physician.

3. The computer-implemented method of claim 2, wherein the received location indicates that the mobile device is in one of a home or an office or a hospital associated with the physician.

4. The computer-implemented method of claim 3, further comprising:
    determining, after selecting the first set of physician metrics, new location information indicating that the mobile device has moved to another one of the home or the office or the hospital; and
    in response to determining the new location information, changing the display of the mobile device to display the second performance data with at least one performance metric of the first set of physician metrics different than a currently displayed performance metric based on the new location information.

5. The method claim 4, wherein the interaction is a screen swipe, the method further comprising:
generating a notification when an update for the second performance data is available.

6. The computer-implemented method of claim 1, further comprising:
receiving confirmation that a user associated with the request has been authenticated to access the first performance data associated with the physician,
wherein the first performance data is obtained based on receiving the confirmation.

7. The method of claim 6, wherein receiving confirmation that the user associated with the request has been authenticated comprises receiving an indication that the user is the physician.

8. The method of claim 1, further comprising:
refreshing the displayed first set of physician metrics periodically to incorporate newly updated data.

9. A system comprising:
a memory device storing instructions therein; and
one or more processors configured to execute the instructions stored in the memory device to:
receive a request via a mobile device for first performance data associated with a physician, the first performance data associated with a period of time;
receive the first performance data and a location of the mobile device;
select, based on the location of the mobile device, a first set of physician metrics of a plurality of sets of physician metrics for display based on the first performance data in a format specific to the mobile device, the plurality of sets of physician metrics including two or more of patient length of stay, cost per stay, mortality rate, readmission rate, drug events, patient recovery time, medication spending, and patient satisfaction associated with the physician;
provide the formatted first set of physician metrics for display on the mobile device;
receive an indication of an interaction with a portion of the mobile device presenting the displayed first set of physician metrics; and
responsive to receiving the indication, switch the first set of physician metrics from using the first performance data to second performance data of a type of performance data different than a type of the first performance data, and displaying the same first set of physician metrics using the second performance data, the types of first and second performance data being selected from physician data, patient data, medicine data, medical procedure data, and hospital data.

10. The system of claim 9, wherein one or more processors, when executing the instructions, are further configured to:
receive an indication that the location of the mobile device is associated with the physician,
wherein the selecting is based on the location being associated with the physician.

11. The system of claim 10, wherein the received location indicates that the mobile device is in one of a home or an office or a hospital associated with the physician.

12. The system of claim 11, wherein one or more processors, when executing the instructions, are further configured to:
determine, after selecting the first set of physician metrics, new location information indicating that the mobile device has moved to another one of the home or the office or the hospital; and
in response to determining the new location information, change the display of the mobile device to display the second performance data with at least one performance metric of the first set of physician metrics different than a currently displayed performance metric based on the new location information.

13. The system of claim 9, wherein one or more processors, when executing the instructions, are further configured to:
receive confirmation that a user associated with the request has been authenticated to access the first performance data associated with the physician,
wherein the first performance data is obtained based on receiving the confirmation.

14. The system of claim 13, wherein receiving confirmation that the user associated with the request has been authenticated comprises receiving an indication that the user is the physician.

15. A non-transitory machine-readable medium comprising instructions stored thereon that, when executed by a computing device, cause a computing device to perform operations comprising:
receiving a request via a mobile device for first performance data associated with a physician, the first performance data associated with a period of time;
receiving the first performance data and a location of the mobile device;
selecting, based on the location of the mobile device, a first set of physician metrics of a plurality of sets of physician metrics for display based on the first performance data in a format specific to the mobile device, the plurality of sets of physician metrics including two or more of patient length of stay, cost per stay, mortality rate, readmission rate, drug events, patient recovery time, medication spending, and patient satisfaction associated with the physician;
providing the formatted first set of physician metrics for display on the mobile device;
receiving an indication of an interaction with a portion of the mobile device presenting the displayed first set of physician metrics; and
responsive to receiving the indication, switching the first set of physician metrics from using the first performance data to second performance data of a type of performance data different than a type of the first performance data, and displaying the same first set of physician metrics using the second performance data, the types of first and second performance data being selected from physician data, patient data, medicine data, medical procedure data, and hospital data.

16. The non-transitory machine-readable medium of claim 15, wherein the operations further comprise:
receiving an indication that the location of the mobile device is associated with the physician,
wherein the selecting is based on the location being associated with the physician.

17. The non-transitory machine-readable medium of claim 16, wherein the received location indicates that the mobile device is in one of a home or an office or a hospital associated with the physician.

18. The non-transitory machine-readable medium of claim 17, wherein the operations further comprise:

determining, after selecting the first set of physician metrics, new location information indicating that the mobile device has moved to another one of the home or the office or the hospital; and in response to determining the new location information, changing the display of the mobile device to display the second performance data with at least one performance metric of the first set of physician metrics different than a currently displayed performance metric based on the new location information.

19. The non-transitory machine-readable medium of claim 15, wherein the operations further comprise:
receiving confirmation that a user associated with the request has been authenticated to access the first performance data associated with the physician,
wherein the first performance data is obtained based on receiving the confirmation.

20. The non-transitory machine-readable medium of claim 19, wherein receiving confirmation that the user associated with the request has been authenticated comprises receiving an indication that the user is the physician.

* * * * *